US011911457B2

(12) United States Patent
Ella et al.

(10) Patent No.: US 11,911,457 B2
(45) Date of Patent: Feb. 27, 2024

(54) PROCESS FOR ENTEROVIRUS PURIFICATION AND INACTIVATION AND VACCINE COMPOSITIONS OBTAINED THEREOF

(71) Applicant: BHARAT BIOTECH INTERNATIONAL LIMITED, Hyderabad (IN)

(72) Inventors: Krishna Murthy Ella, Hyderabad (IN); Vijaya Kumar Daram, Hyderabad (IN)

(73) Assignee: BHARAT BIOTECH INTERNATIONAL LIMITED, Hyderabad (IN)

( * ) Notice: Subject to any disclaimer, the term of this patent is extended or adjusted under 35 U.S.C. 154(b) by 0 days.

(21) Appl. No.: 16/967,451

(22) PCT Filed: Feb. 6, 2019

(86) PCT No.: PCT/IN2019/050095
§ 371 (c)(1),
(2) Date: Aug. 5, 2020

(87) PCT Pub. No.: WO2019/155492
PCT Pub. Date: Aug. 15, 2019

(65) Prior Publication Data

US 2020/0376110 A1 Dec. 3, 2020

(30) Foreign Application Priority Data

Feb. 7, 2018 (IN) ............................ 201841004703

(51) Int. Cl.
*A61K 39/395* (2006.01)
*A61K 39/13* (2006.01)
(Continued)

(52) U.S. Cl.
CPC ................ *A61K 39/13* (2013.01); *C12N 7/00* (2013.01); *A61K 2039/5252* (2013.01);
(Continued)

(58) Field of Classification Search
None
See application file for complete search history.

(56) References Cited

U.S. PATENT DOCUMENTS 4,525,349 A 6/1985 Montagnon et al.
2014/0287043 A1* 9/2014 Kaplan ................ A61K 39/099 424/234.1
2019/0194628 A1* 6/2019 Rao ........................ A61K 39/12

FOREIGN PATENT DOCUMENTS

WO 2003054174 A1 7/2003
WO 2011006823 A1 1/2011
WO 2012171026 A2 12/2012
WO 2016063291 A1 4/2016

OTHER PUBLICATIONS

International Search Report dated Apr. 25, 2019 for PCT/IN2019/050095.
(Continued)

*Primary Examiner* — M Franco G Salvoza
(74) *Attorney, Agent, or Firm* — Schmeiser, Olsen & Watts, LLP (57) ABSTRACT

The present invention pertains to the field of industrial scale inactivation of various enteroviruses and large and industrial scale production of enterovirus vaccine compositions and combinations of various enteroviruses so obtained.

15 Claims, 7 Drawing Sheets

Single Chromatography: Poliovirus Type-1

Quality of the PV-1 protein by SDS PAGE

(51) Int. Cl.
    *C12N 7/00*    (2006.01)
    *A61K 39/00*   (2006.01)
(52) U.S. Cl.
    CPC .............. *C12N 2770/32634* (2013.01); *C12N 2770/32652* (2013.01); *C12N 2770/32663* (2013.01)

(56) References Cited

OTHER PUBLICATIONS

Written Opinion dated Apr. 25, 2019 for PCT/IN2019/050095.
Tano Y et al, Aug. 2007. "Antigenic characterization of a formalin-inactivated poliovirus vaccine derived from live-attenuated Sabin strains" Vaccine, vol. 25, No. 41, p. 7041-7046.
Salk et. al., "Formaldehyde Treatment and Safety Testing of Experimental Poliomyelitis Vaccines", American Journal of Public Health, vol. 44, No. 5, May 1954.
Goldblum et. al., Production of Formalinized Poliomyelitis Vaccine (Salk-Type) on a Semi-Industrial Scale, The Virus Laboratory, Ministry of Health, Tel Aviv-Yaffo, Israel, 1957, 17, 1001-1023.
Hampton J.W.F. et. al., The Use of Ultra-Violet Light as an Additional Means of Inactivation of Formalinized Vaccine, Laboratories of the Poliomyelitis Research Foundation, Johannesburg, and the Council for Scientific and Industrial Research and University of Capetown Virus Research Unit, University of Capetown, pp. 266-270.
Martin et. al., Characterization of formaldehyde-inactivated poliovirus preparations made from live-attenuated strains, Journal of General Virology (2003), 84, 1781-1788.

\* cited by examiner

Single Chromatography:
Poliovirus Type-1

Figure 1:
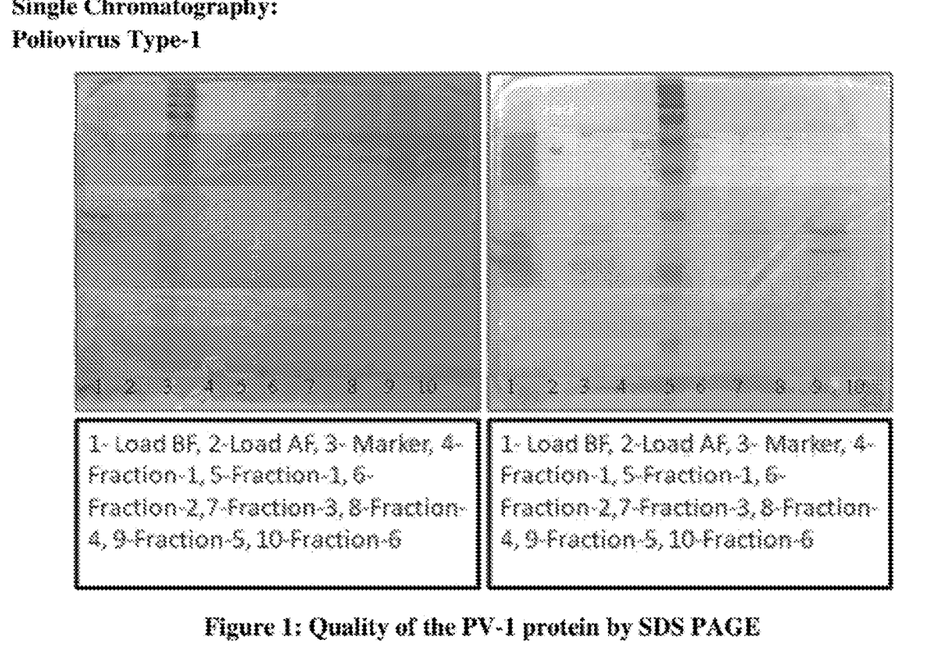

Figure 1: Quality of the PV-1 protein by SDS PAGE

Figure 2:
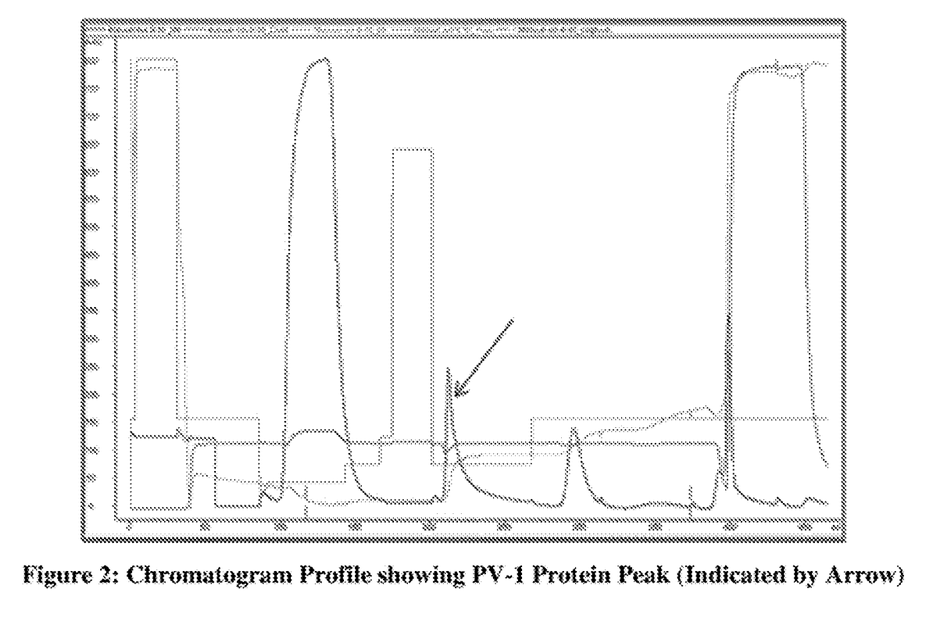
Figure 2: Chromatogram Profile showing PV-1 Protein Peak (Indicated by Arrow)

Single Chromatography:
Poliovirus Type-3

Figure 3:
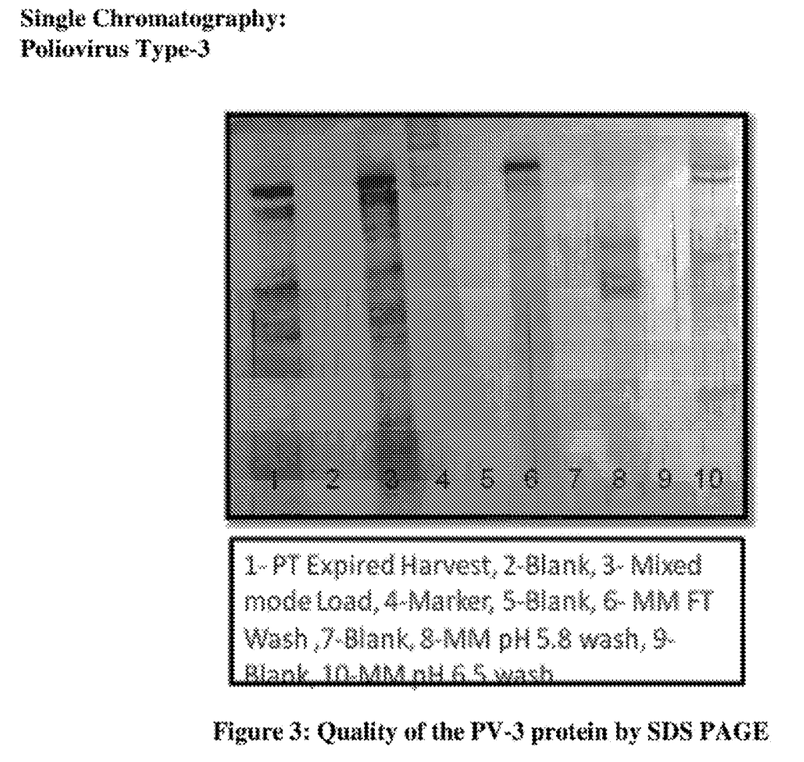
Figure 4:
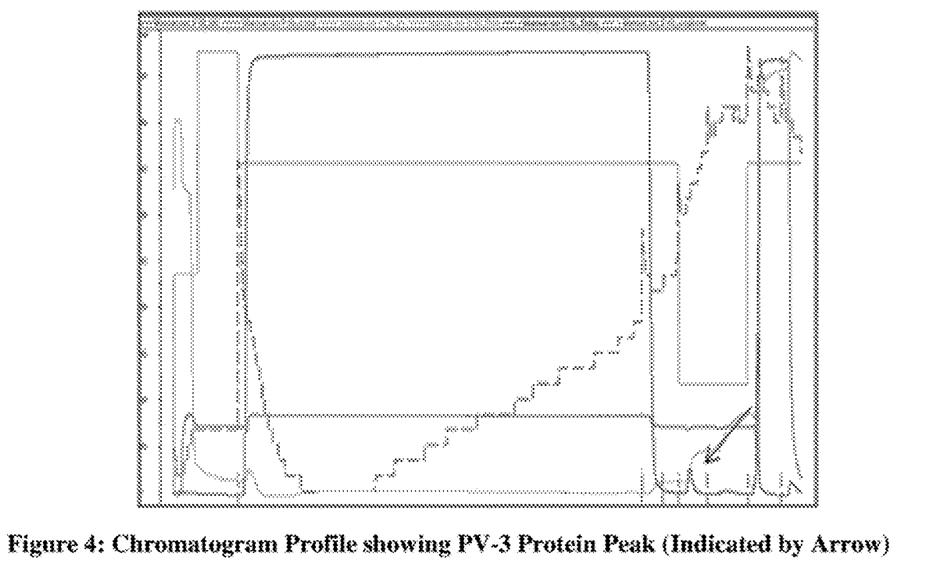

Figure 3: Quality of the PV-3 protein by SDS PAGE

Figure 5:
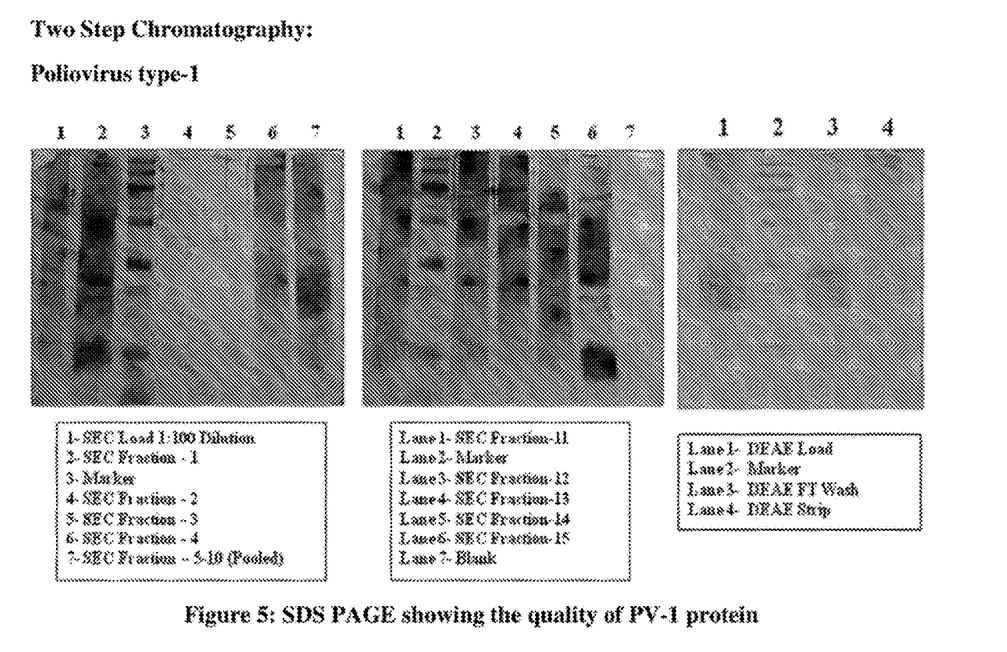

Figure 5: SDS PAGE showing the quality of PV-1 protein

Figure 6:
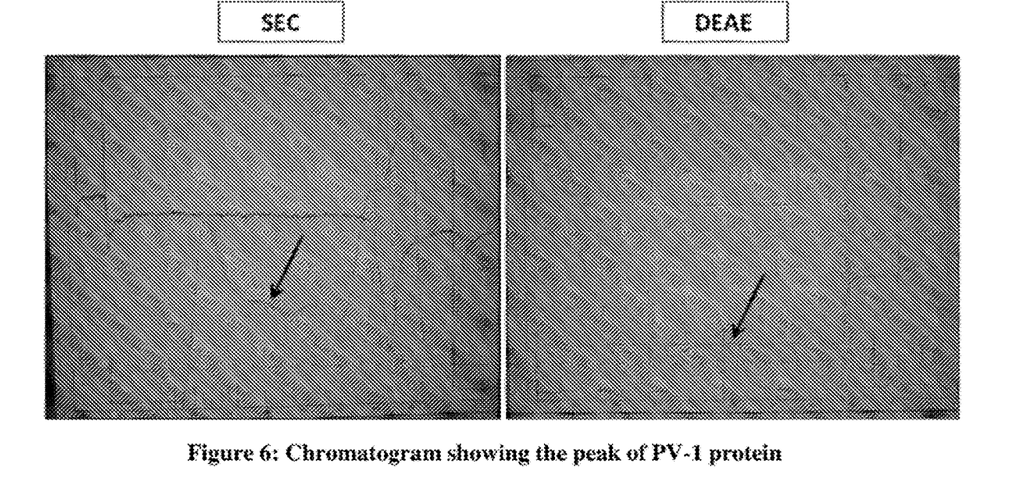

Figure 6: Chromatogram showing the peak of PV-1 prot

Two Step Chromatography:

Poliovirus type-2

Figure 7:
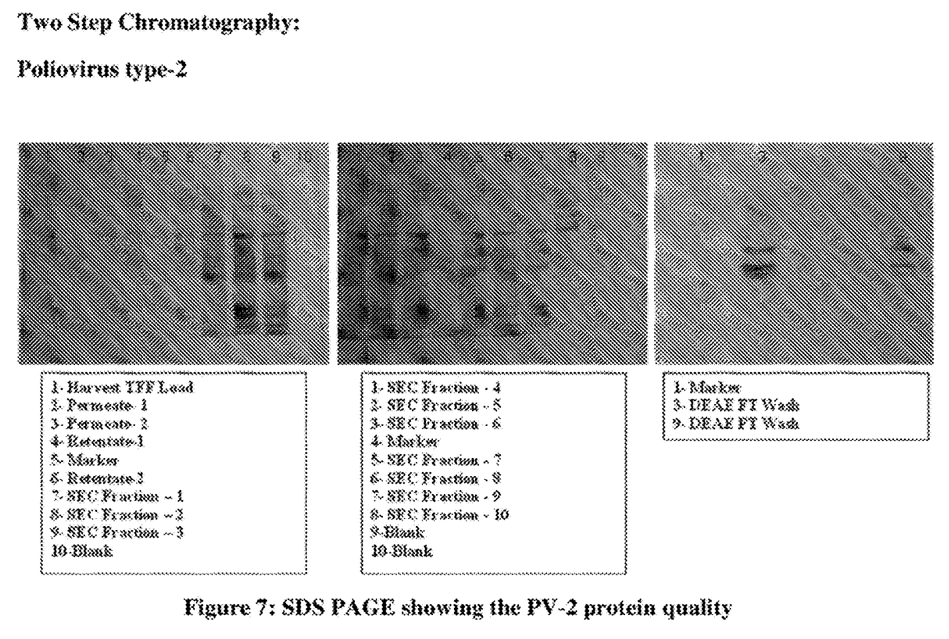

Figure 7: SDS PAGE showing the PV-2 protein quality

Two Step Chromatography:

Poliovirus type-3

Figure 8:
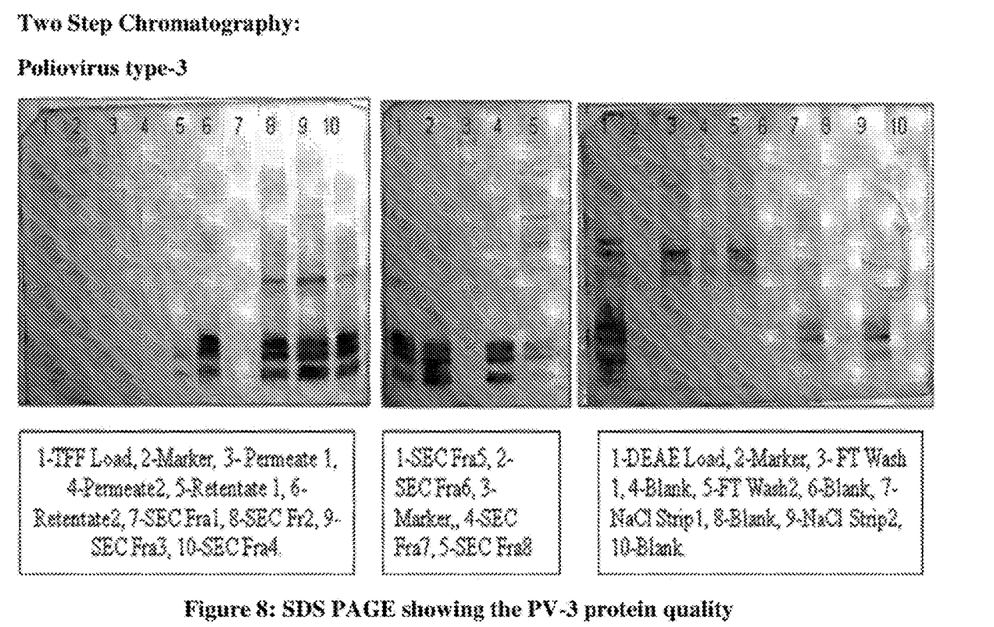
Figure 9:
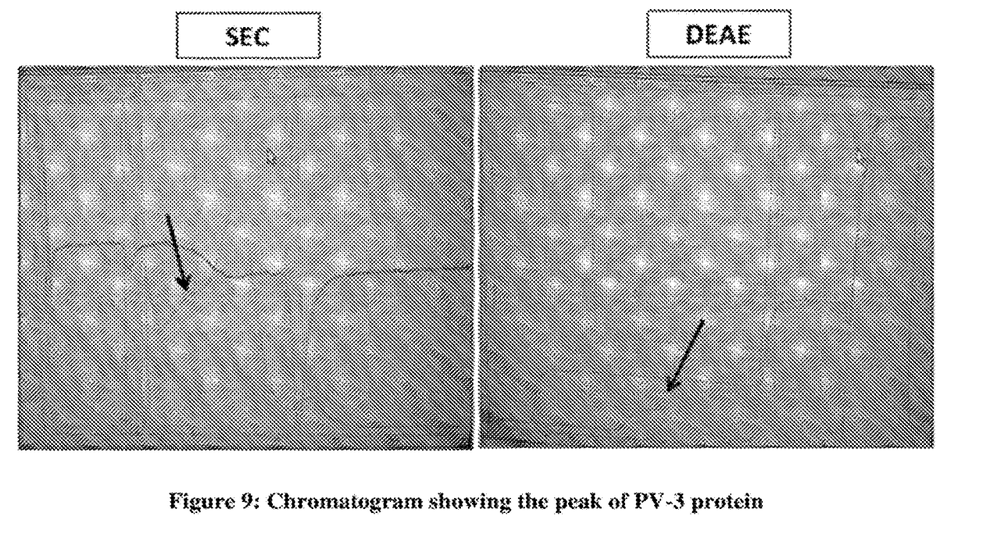

Figure 8: SDS PAGE showing the PV-3 protein quality

Figure 10:
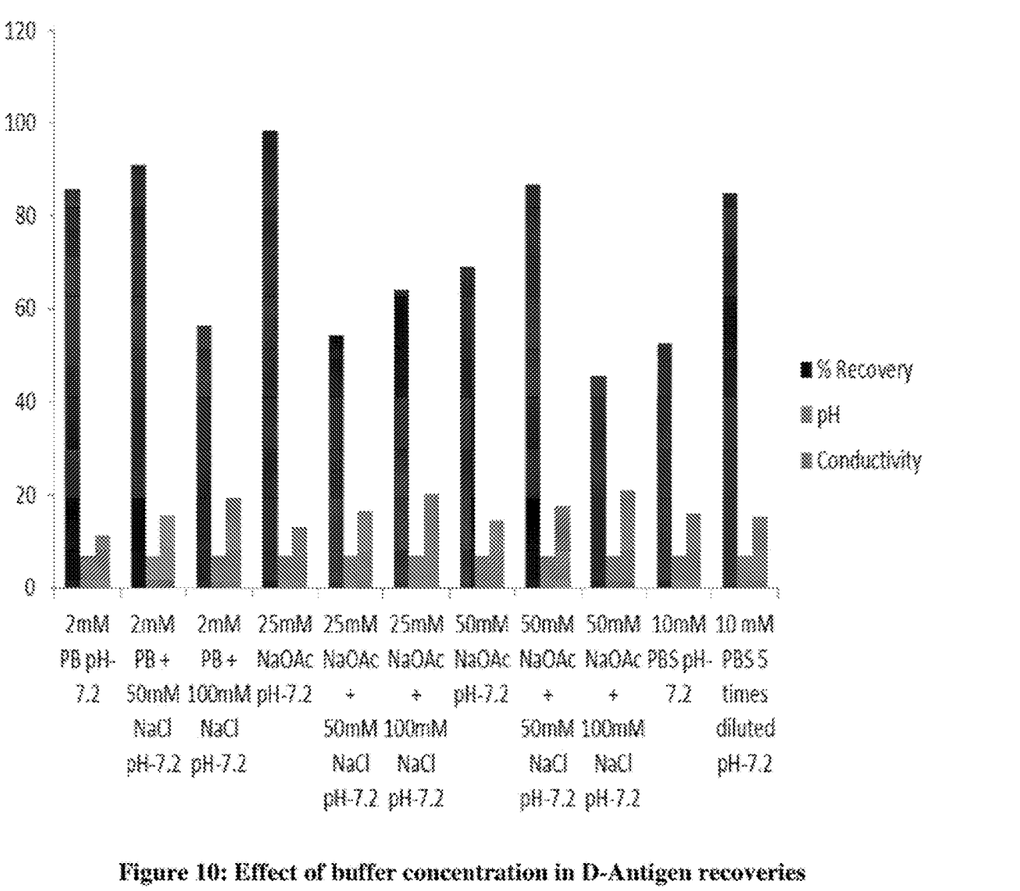

Figure 10: Effect of buffer concentration in D-Antigen recoveries

Figure 11:
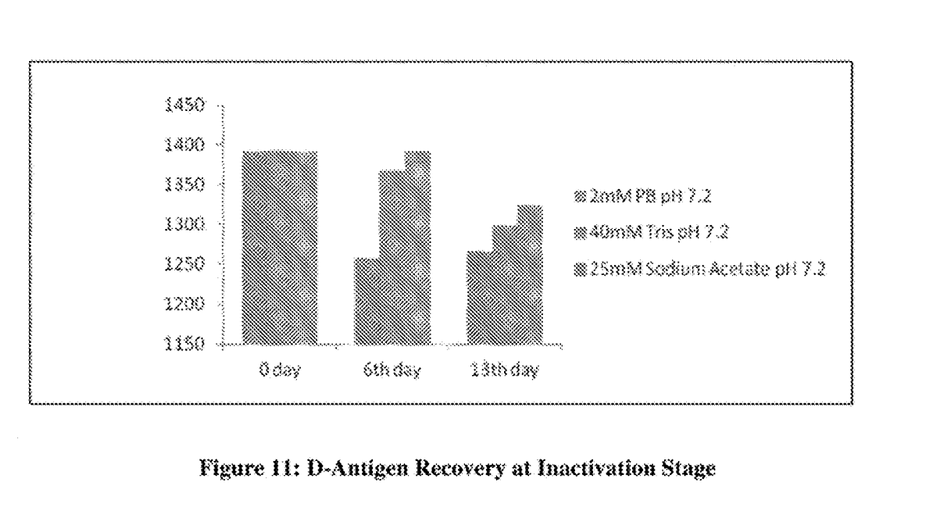

Figure 11: D-Antigen Recovery at Inactivation Stage

Figure 12:
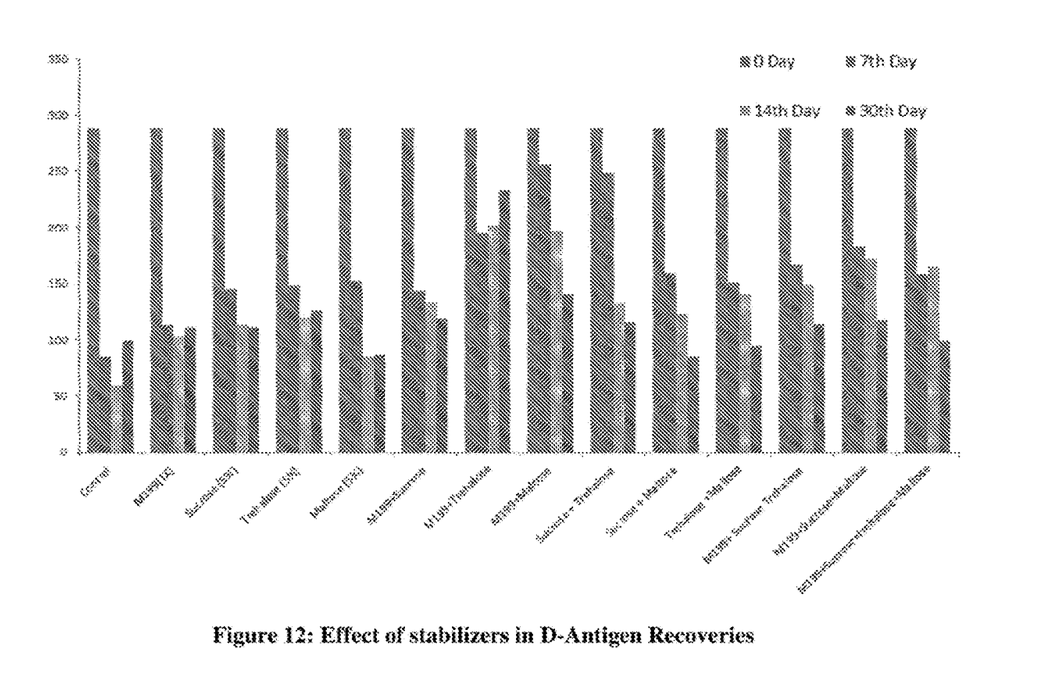

Figure 12: Effect of stabilizers in D-Antigen Recoveries

PROCESS FOR ENTEROVIRUS PURIFICATION AND INACTIVATION AND VACCINE COMPOSITIONS OBTAINED THEREOF

CROSS-REFERENCE TO RELATED APPLICATIONS

This application claims priority to PCT Application No. PCT/IN2019/050095, having a filing date of Feb. 6, 2019, based on IN 201841004703, having a filing date of Feb. 7, 2018, the entire contents both of which are hereby incorporated by reference.

FIELD OF TECHNOLOGY

The following relates to industrial scale production of Enteroviral (D-Antigen) particles with high production yield and preparation of enterovirus vaccine compositions from such Enteroviral (D-Antigen) particles. More particularly, embodiments of the invention relate to industrial scale inactivation of various enteroviruses and production of enterovirus vaccine compositions of various enteroviruses so obtained on large and industrial scale.

BACKGROUND

Enteroviruses are positive-sense single-stranded RNA viruses that cause several human and mammalian diseases. Seventy one human enterovirus serotypes have been distinguished on the basis of antibody neutralization tests. Enteroviruses affect millions of people worldwide each year, and are often found in the respiratory secretions (e.g., saliva, sputum, or nasal mucus) and stool of an infected person. Enteroviruses can be further categorized into polio enteroviruses and 64 non-polio enteroviruses that can cause disease in humans. Non-polio enteroviruses can further be divided into: 23 Coxsackie A viruses, 6 Coxsackie viruses, 28 echoviruses, and 5 other enteroviruses.

Poliomyelitis (also known as polio or infantile paralysis) is a highly infectious, acute paralytic disease, caused by poliovirus. Poliovirus is a member of enterovirus subgroup, family Picornaviridae. Poliovirus infections only occur in humans, more commonly in infants and young children. The poliovirus is mainly transmitted through the faecal-oral route or less frequently, by a common vehicle (e.g. contaminated water or food). It multiplies in the intestine and then invades the nervous system leading to paralysis.

About 72% of the infected people do not show any visible symptoms, while about 24% people show flu-like symptoms lasting for 2-5 days. Flu-like symptoms includes sore throat, fever, tiredness, nausea, headache, vomiting, stiffness in the neck, stomach pain and pain in the limbs. About 1% of people have weakness or paralysis in their arms, legs, or both. In a small proportion of cases, the disease causes paralysis, which is often permanent. About 2%-10% people who have paralysis from polio die because the virus affects the muscles that help them breathe. Post-polio syndrome, which may occur 15-40 years after the recovery from polio, is also possible occurrence. There is no cure for polio, thus prophylaxis via immunization is the only option. Almost all children (99%) who get all the recommended doses of the vaccine are protected from polio.

Two types of poliovirus vaccines namely Oral Polio Vaccines (OPV) and Inactivated Polio Vaccines (IPV) are used for the disease control. OPV (also called Sabin vaccine, based on Albert Sabin's live-attenuated vaccines developed in 1956) is a magnesium chloride stabilized preparation of live attenuated polio viruses of the Sabin strains type 1 (LS-c, 2ab), type 2 (P712, Ch, 2ab) and type 3 (Leon 12ab). Each dose of OPV contains residual amounts (25 μg) of antibiotics including streptomycin and neomycin. Adjuvants or preservatives are not used in OPV.

IPV (also called Salk vaccine, based on formalin inactivated vaccines by Jonas Salk in 1953) contains three poliovirus strains, Mahoney type 1, MEF-1 (Middle East Forces) type 2 and Saukett type 3. The viruses are grown either in Vero cells or human diploid (MRC-5) cells and then concentrated, purified and inactivated in formaldehyde. Each dose of IPV contains 40 D antigen units of type 1, 8 D antigen units of type 2 and 32 D antigen units of type 3. Trace amounts of antibiotics, such as streptomycin, neomycin and polymyxin B are also used in IPV. These antibiotics prevent the spread of virus to the central nervous system in case of infection. Some IPV also contain 2-phenoxyethanol as a preservative. IPV is administered either intramuscular or subcutaneous.

Since OPV induces both a systemic and mucosal immune response, it is the obvious choice for the poliomyelitis eradication program. The OPV vaccine is easier to administrate, induces long-lasting protective systemic, humoral and cellular immunity as well as local mucosal resistance to poliovirus infection. However, the major risks of OPV vaccination are the appearance of Vaccine-Associated Paralytic Poliomyelitis cases (VAPP) and the emergence of Vaccine Derived Polioviruses strains.

On the other hand, major advantage of IPV over OPV is that it eliminates the risk of VAPP, since it doesn't contain any 'live attenuated' virus. Therefore, IPV is one of the safest vaccines in use, since no serious systemic adverse reactions has been shown to follow vaccination. IPV also triggers an excellent protective immune response and is highly effective in preventing paralytic disease caused by all three types of poliovirus. IPV however, induces low levels of immunity in intestine. Administering IPV requires trained health workers, sterile injection equipment and procedures. Furthermore, IPV is almost five times more expensive than OPV due to the complexity involved in the process of production of IPV.

Salk et. al., "*Formaldehyde Treatment and Safety Testing of Experimental Poliomyelitis Vaccines*", American Journal of Public Health, Volume 44, No. 5, May 1954, teaches formaldehyde inactivation of the poliovirus, in which the polioviruses are grown on monkey kidney tissue, filtered and then passed through bacteria retaining filter pad. $CO_2$ is removed from the filtered solution under partial vacuum in a closed system to ensure constant pH, and adjusted to 7.0 during the inactivation process. The sample material was then treated with formalin and thereafter titrated for residual infectivity on each successive 24 hours. It was observed that 1:4000 formalin was able to reduce the inactivate 50% of the poliovirus (0.5 mL sample) within 3 days, at 7.0 pH. The time required for higher volume of poliovirus was higher as compared to 0.5 mL quantity of poliovirus.

Goldblum et. al., PRODUCTION OF FORMALINIZED POLIOMYELITIS VACCINE (SALK-TYPE) ON A SEMI-INDUSTRIAL SCALE, The Virus Laboratory, Ministry of Health, Tel Aviv-Yaffo, Israel, 1957, 17, 1001-1023, teaches a method of production of formalinized poliomyelitis vaccine (Salk-Type) on a semi-industrial scale. The poliovirus was grown on monkey kidney cell suspension. The virus suspension pool (19 L) so obtained was then put to a series of filtration under 0.2-03 atmospheric pressure through corning tubular filters in closed system. The pool was adjusted to pH at 7.0 and slow continuous filtration was carried out overnight. The pool was then pre-heated in water bath at 37° C. and formalin was added to a final concentration of 1:4000. A 1:200 dilution of formalin (37% formaldehyde) was added at the rate of 50 mL per 950 mL of virus suspension under vigorous shaking. A 200 mL sample was drawn out and stored in eight equal pilot bottles for four days for inactivation. The solutions were then treated with 0.5 mL of a 1/16 dilution of 35% concentrate of Sodium bisulfite for neutralization. Each neutralized sample was then treated with 20 vol. of PBS at 4° C. for four hours. PBS was then changed and dialysis was continued overnight. Further filtration was carried out at the rate of 5-5.5 litres of filtrate per hour. Proper samples of inactivated poliovirus were obtained. The total time of inactivation in routine production of vaccine took 12 days.

Hampton J. W. F. et. al., *THE USE OF ULTRA-VIOLET LIGHT AS AN ADDITIONAL MEANS OF INACTIVATION OF FORMALINIZED VACCINE*, Laboratories of the Poliomyelitis Research Foundation, Johannesburg, and the Council for Scientific and Industrial Research and University of Capetown Virus Research Unit, University of Capetown, pp. 266-270, teaches irradiation of formalinized vaccine, as an additional inactivation process, using a simple irradiator. In this method, tissue culture harvest of poliovirus was filtered by two passes through ultra-fine sintered glass-filters. Thereafter virus assay was carried out in roller-tube cultures of trypsinized monkey-kidney cells. The cell suspension was then irradiated via monochromatic ultra-violet light. The results showed that formaldehyde inactivated virus suspension, when further subjected to a second method of inactivation (irradiation), only had little effect on its antigenicity potency.

Martin et. al., *Characterization of formaldehyde-inactivated poliovirus preparations made from live-attenuated strains*, Journal of General Virology (2003), 84, 1781-1788, teaches the laboratory scale production of formaldehyde inactivated poliovirus (from Sabin strains) and the effect of formaldehyde on virus infectivity and immunogenicity. Virus stocks of poliovirus were prepared by infecting HEp-2c cells at high MOI (>10 p.f.u. ml21) at 35° C. in MEM without foetal calf serum. Supernatants were collected after 24-48 hours and purified by ultracentrifugation through 15-45% sucrose gradients. Sucrose gradient-purified virus preparations were re-suspended in an inactivation medium. The virus pool was then filtered through a 0.2 µm filter to remove viral aggregates. The purified virus solutions were treated with 1:4000 dilution of formaldehyde. Inactivation was carried out for 12 days at 37° C. in a constant-temperature water-bath. Viruses were again filtered through a 0.2 µm filter at sixth day. It was concluded that the kinetics of inactivation of virus infectivity with formaldehyde was very similar to that of the Sabin strains. Further that formaldehyde treatment had only slight effect on immunogenicity.

U.S. Pat. No. 4,525,349 (Montagnon et. al.) teaches a process of large scale production of poliomyelitis vaccine wherein the viral strains are inoculated into the VERO cell medium. The viral suspension is harvested from the culture medium and filtered on a 0.22 micron cellulose ester membrane. It is then subjected to ultrafiltration and concentrated. The concentrated suspension is then placed on a gel filtration column containing an agarose gel at pH 7 with a 0.04 M phosphate buffer. The effluent suspension is put onto an ion exchange chromatography. The concentrated and purified viral suspension is then diluted and filtered on 0.22 micron cellulose ester membrane. It is heated to 37° C. and inactivated by adding formol solution to achieve a concentration of 1 per 4000.

International Publication No. WO2016063291 (Dhere R. M. et. al.) application teaches a method for preparing IPV containing Salk or Sabin polioviruses in which the polioviruses were purified, then stabilized by adding M-199 medium containing glycine, then inactivated by using formaldehyde 1:4000 dilution at 37° C. for 5-13 days in presence of TRIS buffer at a concentration of 40 mM, and finally adsorbed to Alum hydroxide adjuvant. It further teaches that use of Phosphate buffer in place of TRIS buffer actually reduced the D-antigen recovery by 10-folds, thereby discouraging the use of Phosphate buffer in the process of IPV production.

The need of production of IPV at industrial level with minimum cost input arose since the World Health Organisation (WHO) proposed Global poliomyelitis eradication to its member states in 1988, establishing strategic plan for polio eradication, certification of regions, OPV cessation and post-OPV phase. At the time, poliomyelitis was endemic in more than 125 countries causing permanent paralysis to more than 350,000 children every year. Today, transmission of wild poliovirus is at its lowest levels ever, with endemic transmission only occurring in parts of Pakistan, Afghanistan and Nigeria. Polio Eradication and Endgame Strategic Plan 2013-18 was developed later by Global Polio Eradication Initiative (GPEI) in response to a directive of the World Health Assembly to make the world free from polio by 2018. The comprehensive long term strategy had objectives such as: detection and interruption of all poliovirus transmission; strengthening immunisation systems; and withdrawing OPV by year 2020.

At its meeting in October 2016, the Strategic Advisory Group of Experts on immunization (SAGE) which is the principal advisory group to WHO for vaccines and immunization, noted both the reduction in supplies of IPV, due to technical difficulties that manufacturers have encountered in scaling up production, and the expectation that the global vaccine supply will remain fragile through 2018.

This has rendered the vaccine manufacturers to focus on the production of IPV in large quantity so that the global demand can be met within the stipulated time. The success of post-OPV phase largely depends on the accessibility and affordability of IPV. However, at present the cost of production of IPV is much higher than that of OPV. The technical difficulty in scaling up the laboratory methods of inactivation of IPV and further large scale production of IPV presents serious challenge before the vaccine manufacturing industry. The absence of technology for scaling up of IPV, so that recovery of IPV is more at industrial level, with reduction in cost of manufacturing has not been solved yet.

Embodiments of the present invention provide for an improved technical process of industrial scale production of IPV, wherein the recovery of IPV is high. The cost of production of IPV will reduce significantly, making embodiments of the present invention the most preferred choice of industrial production. Embodiments of the present invention is technical advancement in the field since it teaches a novel process by which large scale production of IPV is carried out with significantly lower cost. Embodiments of the invention further solve the issue of accessibility and affordability of IPV vaccines around the world.

SUMMARY

An aspect relates to a process of purification and inactivation of enteroviruses at industrial scale that gives higher level of recovery of immunogenic antigens.

Another objective of embodiments of the invention is to provide a process of purification and inactivation of poliovirus at industrial scale that gives higher level of recovery of immunogenic antigens.

Another objective of embodiments of the invention is to provide a process of vaccine manufacturing at industrial level at reduced cost.

Yet another objective of embodiments of the invention is to provide vaccine compositions comprising Enteroviral (D-Antigen) particles obtained from the improved method of purification and inactivation of various enteroviruses at industrial scale.

Yet another objective of embodiments of the invention is to provide vaccine compositions comprising poliovirus (D-antigen) particles obtained from the improved method of purification and inactivation of poliovirus at industrial scale.

Another objective of embodiments of the invention is to provide vaccine compositions comprising poliovirus (D-antigen) particles obtained from the improved method of purification and inactivation of poliovirus that is stable and shows high antigenic value.

Embodiments of the present invention provides for the technical advancement in the large and industrial scale cost-effective production methods of various Enteroviruses vaccines and its various compositions thereof, which are stable, safe and effective to use. Embodiments of the present invention provides for high recovery of antigenic components, such as D-antigens under the process disclosed herein.

In one aspect of embodiments of the the invention, there is provided a method for producing Enteroviral (D-Antigen) particles useful for preparation of vaccine compositions, wherein the method comprises the steps of:

a. producing Enteroviral particles in Vero cells;
b. purification of the Enteroviral particles either by Single Step Chromatography or Two Step Chromatography;
c. stabilization of purified Enteroviral particles; and
d. inactivation of the Enteroviral particles to obtain Enteroviral (D-Antigen) particles; wherein the said method comprises addition of one or more excipient including stabilizers and adjuvants before or after the inactivation step, and wherein the D-antigen recovery is in the range of 80% to 99%.

In some embodiments of the invention, in the above described method for producing Enteroviral (D-Antigen) particles, the Single Step Chromatography is carried by using a single column prepared by mixing one or more ion exchange resin with one or more hydrophobic resin.

In other embodiments of the invention, in the above described method for producing Enteroviral (D-Antigen) particles, the Two Step Chromatography is carried by first running Size Exclusion Chromatography or Gel Filtration Chromatography followed by ion exchange chromatography.

In yet other embodiments of the invention, in the above described method for producing Enteroviral (D-Antigen) particles, the inactivation process is selected from heat inactivation, chemical inactivation, irradiation or UV treatment. In some embodiments, the chemical inactivation is carried by using one or more chemicals selected from a group of formalin, beta-propiolactone (BPL), hydrogen peroxide, glutaraldehyde, N-acetyl ethyleneimine, binary ethyleneimine, tertiary ethyleneimine, ascorbic acid, caprylic acid, psolarens or a detergent; and an inactivation buffer.

In some embodiment, the inactivation is carried by addition of formalin and inactivation buffer selected from a group comprising phosphate buffer, TRIS, Sodium Acetate, TBS, MOPS, HEPES or bicarbonate buffer in presence or absence of salt. In some embodiment, the inactivation buffer comprises a buffer selected from a group of phosphate buffer, combinations of phosphate buffer and TRIS, sodium acetate, salts with sodium acetate, TBS, MOPS, HEPES and bicarbonate buffers; M-199; glycine and tween 80.

In some embodiment, in the formalin inactivation the phosphate buffer is used at a concentration in the range of 1 mM-10 mM, in particular 2 mM with or without NaCl in the pH range of 6.0 to 7.5, in particular at 7.2. In some other embodiment, the phosphate buffer is used at a concentration in the range of 1 mM-10 mM, in particular 2 mM along with saline at a concentration of 10 mM in the pH range of 6.0 to 7.5, in particular at 7.2.

In some embodiment, in the formalin inactivation, sodium acetate buffer is used at a concentration in the range of 20 mM-50 mM, in particular 25 mM with or without NaCl in the pH range of 6.0 to 7.5, in particular at 7.2. In some embodiment, sodium acetate buffer is used at a concentration of 25 mM having the pH of about 7.2.

In some embodiment, in the above described method for producing Enteroviral (D-Antigen) particles, the used stabilizers are selected from the group of sucrose, maltose, trehalose, human serum albumin, and M199.

In some embodiment, in the above described method for producing Enteroviral (D-Antigen) particles, the excipient is added before the inactivation step.

In some embodiment, in the above described method for producing Enteroviral (D-Antigen) particles, the inactivation is carried by an inactivation buffer comprising a buffer selected from a group of phosphate buffer, combinations of phosphate buffer and TRIS, sodium acetate, salts with sodium acetate, TBS, MOPS, HEPES or bicarbonate buffers; M-199 or M-199 in combination with HEPES; glycine and tween 80. In some embodiment, the phosphate buffer is used at a concentration in the range of 1 mM-10 mM, in particular 2 mM at the pH range of 6.0 to 7.5, in particular at 7.2 with one or more stabilizer.

In some embodiment, in the above described method for producing Enteroviral (D-Antigen) particles, the stabilizer is selected from a group comprising sucrose in 5% w/v concentration, M199 in 9.9 g/L concentration, trehalose in 5% w/v concentration, maltose in 5% w/v concentration and human serum albumin in 5% w/v concentration. In some embodiment, the stabililizer is M199 in 9.9 g/L concentration and trehalose in 5% w/v concentration.

In some embodiment, there is provided a method for producing Enteroviral (D-Antigen) particles useful for preparation of vaccine compositions, wherein the Enteroviral particles are of polioviruses. In some embodiment, the polioviruses are Sabin serotypes 1, 2 and 3. In some other embodiment, the polioviruses are Sabin serotypes IPV type 1 (Sabin-1 strain), IPV type 2 (Sabin-2 strain), and/or IPV type 3 (Sabin-3strain).

In another aspect of embodiments of the the invention, there is provided a method for preparing a dose reduced inactivated Polio vaccine containing Sabin polioviruses comprises the steps of:

a. producing polioviruses in Vero cells;
b. purification of the polioviruses;
c. stabilization of purified polioviruses by addition of M-199 medium containing glycine and tween 80;
d. inactivation of the polio viruses by using formaldehyde 0.025% at 37° C. for 13 days in presence of Phosphate buffer with saline at a concentration between 2 mM to 10 mM or Sodium acetate (20 mM-30 mM) to reduce aggregation of the poliovirus particles thereby reducing the D-antigen losses post inactivation by greater than 90% as compared to other buffers; and e. formulating the said polio vaccine.

BRIEF DESCRIPTION

Some of the embodiments will be described in detail, with references to the following Figures, wherein like designations denote like members, wherein:

FIG. 1: Quality of the Poliovirus-1 protein by SDS PAGE after single chromatography: Column 1-10;

FIG. 2: Chromatogram Profile showing Poliovirus-1 Protein Peak (Indicated by Arrow) after single chromatography;

FIG. 3: Quality of the Poliovirus-3 protein by SDS PAGE after single chromatography: Column 1-10;

FIG. 4: Chromatogram Profile showing Poliovirus-3 Protein Peak (Indicated by Arrow) after single chromatography;

FIG. 5: SDS PAGE showing the quality of Poliovirus-1 protein for two-step chromatography;

FIG. 6: Chromatogram showing the peak of Poliovirus-1 protein for two-step chromatography;

FIG. 7: SDS PAGE showing the quality of Poliovirus-2 protein for two-step chromatography;

FIG. 8: SDS PAGE showing the quality of Poliovirus-3 protein for two-step chromatography;

FIG. 9: Chromatogram showing the peak of Poliovirus-3 protein for two-step chromatography;

FIG. 10: Effect of buffer concentration in D-Antigen recoveries;

FIG. 11: D-Antigen Recovery during Inactivation Stages; and

FIG. 12: Effect of stabilizers in D-Antigen Recovery.

DETAILED DESCRIPTION

Embodiments of the present invention disclose a novel process for large and industrial scale production of stable and effective immunogenic compositions for conferring protection against various Enteroviruses, that cause paralytic poliomyelitis, aseptic meningitis, febrile illness, rash, myopericarditis, epidemic pleurodynia, hand foot and mouth disease (by EV71), epidemic conjunctivitis (by EV70), Polio-like illness, herpangina, acute hemorrhagic conjunctivitis, severe neonatal disease, Bornholm disease, and encephalitis. Combination vaccine(s) comprising of two or more immunogenic elements selected from various Enteroviruses can be included against wide protection against Enteroviruses. All the methods mentioned in embodiments of the the invention are applicable to any genotype or genotypic variants/serotypes/strains of Enteroviruses.

In one aspect of embodiments of the the invention, there is provided a method for producing Enteroviral (D-Antigen) particles useful for preparation of vaccine compositions, wherein the method comprises the steps of:
a. producing Enteroviral particles in Vero cells;
b. purification of the Enteroviral particles either by Single Step Chromatography or Two Step Chromatography;
c. stabilization of purified Enteroviral particles; and
d. inactivation of the Enteroviral particles to obtain Enteroviral (D-Antigen) particles; wherein the said method comprises addition of one or more excipient including stabilizers and adjuvants before or after the inactivation step, and wherein the D-antigen recovery is in the range of 80% to 99%.

In some embodiments of the invention, in the above described method for producing Enteroviral (D-Antigen) particles, the Single Step Chromatography is carried by using a single column prepared by mixing one or more ion exchange resin with one or more hydrophobic resin. In some embodiment, the ion exchange resin is anion or/and cation exchanger resins selected from DEAE, QEAE, SP Sepharose, Poly CSX-35 or CM Sepharose; the hydrophobic resin is selected from Butyl 650, Phenyl 650, Butyl Sepharose, phenyl Sepharose or octyl Sepharose.

In other embodiments of the invention, in the above described method for producing Enteroviral (D-Antigen) particles, the Two Step Chromatography is carried by first running Size Exclusion Chromatography or Gel Filtration Chromatography followed by ion exchange chromatography. In some embodiment, purification is done by two step chromatography involving SEC (Size Exclusion Chromatography) using Sepharose CL-6B and (Ion-Exchange Chromatography) IEC-DEAE 650M. In some embodiments, two step column chromatography is carried by running GFC (Gel Filtration Chromatography) containing Sepharose CL-6B followed by Ion exchange containing DEAE 650 Matrix resins.

In yet other embodiments of the invention, in the above described method for producing Enteroviral (D-Antigen) particles, the inactivation process is selected from heat inactivation, chemical inactivation, irradiation or UV treatment. In some embodiments, the chemical inactivation is carried by using one or more chemicals selected from a group of formalin, beta-propiolactone (BPL), hydrogen peroxide, glutaraldehyde, N-acetyl ethyleneimine, binary ethyleneimine, tertiary ethyleneimine, ascorbic acid, caprylic acid, psolarens or a detergent; and an inactivation buffer.

In some embodiment, the inactivation is carried by addition of formalin and inactivation buffer selected from a group comprising phosphate buffer, TRIS, Sodium Acetate, TBS, MOPS, HEPES or bicarbonate buffer in presence or absence of salt. In some embodiment, the inactivation buffer comprises a buffer selected from a group of phosphate buffer, combinations of phosphate buffer and TRIS, Sodium Acetate, salts with sodium acetate, TBS, MOPS, HEPES and bicarbonate buffers; M-199; glycine and tween 80.

In some embodiment, in the formalin inactivation the phosphate buffer is used at a concentration in the range of 1 mM-10 mM, in particular 2 mM with or without NaCl in the pH range of 6.0 to 7.5, in particular at 7.2. In some other embodiment, the phosphate buffer is used at a concentration in the range of 1 mM-10 mM, in particular 2 mM along with saline at a concentration of 10 mM in the pH range of 6.0 to 7.5, in particular at 7.2.

In some embodiment, in the formalin inactivation, sodium acetate buffer is used at a concentration in the range of 20 mM-50 mM, in particular 25 mM with or without NaCl in the pH range of 6.0 to 7.5, in particular at 7.2. In some embodiment, sodium acetate buffer is used at a concentration of 25 mM having the pH of about 7.2.

In some embodiment, in the above described method for producing Enteroviral (D-Antigen) particles, the used stabilizers are selected from the group of sucrose, maltose, trehalose, human serum albumin, and M199.

In some embodiment, in the above described method for producing Enteroviral (D-Antigen) particles, the excipient is added before the inactivation step.

In some embodiment, in the above described method for producing Enteroviral (D-Antigen) particles, the inactivation is carried by an inactivation buffer comprising a buffer selected from a group of phosphate buffer, combinations of phosphate buffer and TRIS, sodium acetate, salts with sodium acetate, TBS, MOPS, HEPES or bicarbonate buffers; M-199 or M-199 in combination with HEPES; glycine and tween 80. In some embodiment, the phosphate buffer is used at a concentration in the range of 1 mM-10 mM, in particular 2 mM at the pH range of 6.0 to 7.5, in particular at 7.2 with one or more stabilizer.

In some embodiments of the invention the inactivation buffer is selected from any one of the following:
a. Base 1+2 mM PB;
b. Base 1+2 mM PB+50 mM NaCl;
c. Base 1+2 mM PB+100 mM NaCl;
d. Base 1+25 mM Sodium acetate;
e. Base 1+25 mM Sodium acetate+50 mM NaCl;
f. Base 1+25 mM Sodium acetate+100 mM NaCl;
g. Base 1+50 mM Sodium acetate;
h. Base 1+50 mM Sodium acetate+50 mM NaCl;
i. Base 1+50 mM Sodium acetate+100 mM NaCl;
j. Base 1+10 mM PBS;
k. Base 1+10 mM PBS (5× Diluted) or
l. Base 1+40 mM Tris;
wherein Base 1 is 1× (9.9 g/L) concentrated M-199 with 0.5% glycine and 0.01% tween 80.

In some embodiment, in the above described method for producing Enteroviral (D-Antigen) particles, the stabilizer is selected from a group comprising sucrose in 5% w/v concentration, M199 in 9.9 g/L concentration, trehalose in 5% w/v concentration, maltose in 5% w/v concentration and human serum albumin in 5% w/v concentration. In some embodiment, the stabilizer is M199 in 9.9 g/L concentration and trehalose in 5% w/v concentration.

In some embodiment, there is provided a method for producing Enteroviral (D-Antigen) particles useful for preparation of vaccine compositions, wherein the Enteroviral particles are of polioviruses. In some embodiment, the polioviruses are Sabin serotypes 1, 2 and 3. In some other embodiment, the polioviruses are Sabin serotypes IPV type 1 (Sabin-1 strain), IPV type 2 (Sabin-2 strain), and/or IPV type 3 (Sabin-3strain).

In another aspect of embodiments of the invention, there is provided a method for preparing a dose reduced inactivated Polio vaccine containing Sabin polioviruses, said method comprises the steps of:

a. producing polioviruses in Vero cells;
b. purification of the polioviruses;
c. stabilization of purified polioviruses by addition of M-199 medium containing glycine and tween 80;
d. inactivation of the polio viruses by using formaldehyde 0.025% at 37° C. for 13 days in presence of Phosphate buffer with saline at a concentration between 2 mM to 10 mM or Sodium acetate (20 mM-30 mM) to reduce aggregation of the poliovirus particles thereby reducing the D-antigen losses post inactivation by greater than 90% as compared to other buffers; and
e. formulating the said polio vaccine.

Enteroviruses can be grown in cell cultures. The cell culture used for enterovirus growth is VERO cell line which is a continuous cell line derived from kidney epithelial cells of African green monkey. Vero cells have received worldwide regulatory acceptance and are preferred to be "production" cell substrates that are used to manufacture the bulk product (vaccine production). VERO cells can conveniently be cultured on cell factories, polyester non woven fabrics or cellulose based beads for increasing the yield of cells. After growth, virions are purified by ultrafiltration and chromatography. Prior to administration to patients, the viruses must be inactivated, and this can be achieved by treatment with formaldehyde. An important aspect of embodiments of the instant invention is that said improved process of purification and inactivation of Enterovirus consists of following steps:

A. Cell Culture

Viruses used in embodiments of the present invention are grown in cell factories or fermenters. After attaining the required cell densities, virus is infected with 0.01 MOI (Multiplicity of Infection) of three serotypes of Enterovirus.

Vero cells derived from African green monkey are used as host cells for the production of Enteroviral antigens. Sabin type polioserotypes-1, 2, 3 were received from National Institute for Biological Standards and Control (NIB SC), UK. The poliovirus Sabin strains is used for infection on Vero cells with 0.01 MOI for the production of Enteroviral virions. Infected Vero Cells are then grown in DMEM (Dulbecco's Modified Eagle Medium) supplemented with 5% New Born Calf Serum. Once the confluency is attained in cell factories, the control cell factory is trypsinized with recombinant trypsin for the cell count. Cell count is performed on Neubauer's heamocytometer and total numbers of cells are calculated. Enteroviral inoculum is calculated using the formula:

Required inoculum=Total Number of Cells×MOI/Virus titer

Viral inoculums is then prepared in DMEM and added to the cell factories for viral adsorption and incubated at 32.5° C. for 60 minutes. After the adsorption, the cell factories are topped up with DMEM and incubated at 32.5° C. for the cytopathic effect to be observed. Once the 90-95% cytopathic effect is observed, the viral harvest is collected and clarified using 0.8+0.45μ capsule filter. The clarified viral harvest further used for downstream processing like concentration, purification and further inactivated with formalin.

B. Two-Step Chromatography (TSC): Purification of the viral harvest by using two step chromatography (Size Exclusion Chromatography) SEC using Sepharose CL-6B and (Ion-Exchange Chromatography) IEC-DEAE 650M.

In some embodiment, the purification of the viral antigens is carried out by two step column chromatography by running GFC (Gel Filtration Chromatography) containing Sepharose CL-6B followed by Ion exchange containing DEAE 650 Matrix resins.

Clarified harvest pool is concentrated to 400×-700× using 2 step tangential flow filtration system with 0.1 $m^2$ and 50 $cm^2$ 100 KDa cassettes and collected the retentate. Cassette is washed with phosphate buffered Saline (10 mM, pH: 7.2); then added the wash sample to retentate and used as load for column chromatography.

The purification is done by GFC using Sepharose CL-6B and then Ion Exchange Chromatography (IEC). Virus peak is collected after passing the 400×-700× TFF concentrate through gel filtration column and collected virus containing peak pool. This is used as a load for DEAE 650M (Weak-Anion exchanger) using Akta purification system (GE Healthcare). Impurities are bound to the column whereas poliovirus are collected in flow-through containing 10 mM phosphate buffer saline. The product quality is high with consistency.

Table 1 below depicts the parameters like height, volume, type of matrix, flow rate and buffers used for the purification of polioviruses:

TABLE 1

Chromatography Column Parameters
Column Parameters

| | SEC | IEC |
|---|---|---|
| Column | XK26/100 | XK16/40 |
| Height | 90-100 cm | 10 cm |
| Bed Volume | 480 mL | 20 mL |
| Matrix | Sepharose CL-6B | DEAE 650M/DEAE Sepharose |
| Linear Flow | 20-30 cm/hr | 150 cm/hr |
| Equilibration Buffer | 10 mM phosphate Buffer + 150 mM NaCl (pH-7.2) | 10 mM phosphate Buffer + 150 mM NaCl (pH-7.2) |

A Stable Bulk Concentrate is obtained, which is mixed with Inactivation Buffer for the process of inactivation.

C. Single Step Chromatography (SSC)

In some embodiment, the purification of the viral harvest is done by single chromatographic column using mixture of two different manufacturer resins that have high salt tolerance. Different anion and cation exchanger resins like DEAE, QEAE, SP Sepharose, Poly CSX-35, CM Sepharose were used in combination with hydrophobic resins like Butyl 650, Phenyl 650, Butyl Sepharose, phenyl Sepharose and octyl Sepharose.

The unique functionality of mixed mode is that, resins have functional surface chemistry synthesized by covalently binding polyethylene imine (PEI) to polymethacrylate beads. The PEI is modified to provide carboxylic acid groups and sulfurous acid groups with strong cation-anion exchange sites similar to sulfurous ion exchange resins which offer enhanced performance and better selectivity than conventional ion exchange media with equivalent capacities. Proteins having similar isoelectric points can be easily separated. The efficiency for removal of impurities is greater in a mixed-mode chromatography with fixed amounts of two different resins there by maintaining uniform pH and solubility throughout the column thus saving the process time. The product recoveries and yields are more in SSC. The single column XK16/40 is prepared by packing the column with hydrophobic resin with cation exchanger. The column height was 5 cm with a bed volume of 10 mL. Column was equilibrated with 0.2 M Sodium acetate buffer (pH 4.88) and purified the viral harvest using the Akta purification system. As the column contains cation exchanger, the enteroviral particles are bound to the column in the pH range of 4.8-5.2. Later they are eluted out in the washes with pH range of 5.2-6.0.

The purified bulk is further concentrated and buffer exchanged using tangential flow filtration using 100 KDa cassette attached to a low shear pump. The concentrated bulk is then stabilized [Stable Concentrated Bulk] using M199 and inactivated.

D. Preparation of Inactivation Buffer

TABLE 2

Inactivation buffer composition

| Composition | Concentration |
|---|---|
| M199 | 1X (9.9 g/L) |
| Glycine | 0.5% |
| Tween 80 | 0.01% |
| Phosphate Buffer | 2 mM PB |
| Phosphate Buffer with saline | 2 mM PBS |
| Sodium Acetate | 25 mM NaOAc |

In some embodiment, 10× concentrated M-199 with 0.5% glycine and 0.01% tween 80 is added to make the final inactivation buffer containing 2 mM PB, 2 mM PBS or 25 mM NaOAc, so as to achieve final concentration of 1× M199. Adding M-199 medium containing glycine (5 gm/L) to mixture of the Stable Concentrated Bulk.

Inactivation buffer to be used during formaldehyde inactivation can be selected from the group of PB, PB with salt, Combination of PB and TRIS, Sodium acetate and various concentrations of salt with sodium acetate. Other buffers used for inactivation of viruses include TBS, MOPS, HEPES and bicarbonate buffers within a range of 1 mM-100 mM.

E. Preparation of Incubating Bulk Mixture

Stable Concentrated Bulk of Enterovirus such as Sabin IPV Type-1 or Type-2 or Type-3 purified bulk is mixed with 2 mM Phosphate buffer having pH 7.2, 10 mM Phosphate Buffer with Saline pH 7.2 (5× diluted in inactivation) and 25 mM Sodium Acetate pH 7.2 to obtain Incubating Bulk Mixture.

F. Inactivation

In some embodiment, the Incubating Bulk Mixture is then treated with 0.025% formaldehyde while mixing, at 37° C. from 0 to 13 days on magnetic stirrer. The formalin inactivation with PB buffer occurs in the presence of saline. Post-incubation mixture is thereafter subjected to intermediate 0.22µ filtration on day 6 and final filtration on day 13, storing the Final Bulk so obtained at −20° C.

Reports and literature are available that poliovirus gets completely inactivated with formaldehyde at the concentration of 1:4000 at 37° C. in 12 days. It is also observed that mice showed no paralysis after inactivation with formalin after 12 days. The absence of infectious virus in sequential aliquots and inactivated samples was confirmed by virus titration assays in Vero cells and by the addition and passage of treated virus samples on Vero cell monolayers for period upto 21 days.

The formalin inactivation and formulation with excipients results in D-Antigen recovery post-inactivation more than 90%. Different excipients like sucrose, maltose, trehalose, M199, HSA and PEG were used in combinations at 2-8° C., RT and 37° C. Combination of sucrose and trehalose was found to show stable D-antigen at 37° C.

This inactivation process used in embodiments of the present invention gives higher D-Antigen recoveries due to lower salt concentration. When higher salt concentrations are used in buffers, the viral particle aggregates are formed decreasing the stability of D-Antigen during the inactivation period.

In some embodiment, the viruses are inactivated either by heat, gamma irradiation, and ultra violet light or by chemical means. Chemical inactivating agents are selected from the following list which includes but is not limited to: formalin, beta-propiolactone, hydrogen peroxide, glutaraldehyde, N-acetylethyleneimine, binary ethyleneimine, tertiary ethyleneimine, ascorbic acid, caprylic acid, psolarens, detergents including non-ionic detergents etc. is added to a virus suspension to inactivate the Enteroviruses. Enteroviruses can also be inactivated by using gamma irradiation.

G. Vaccine Formulations

Various vaccine formulations are prepared from the antigens recovered from the process as disclosed under embodiments of the invention. In some embodiment, the vaccine formulations prepared according to embodiments of the invention include pharmaceutical excipients such as stabilizers, adjuvants and the like. The vaccine formulations are prepared with or without stabilizers. Stabilizers may be selected from a range of stabilizers acceptable for the use in vaccine for human use. The vaccine formulations can be prepared with or without the use of adjuvants. The vaccine formulations can be a single dose or multi dose vaccine formulations.

Further, a combination of vaccine formulations can be prepared, where in IPV may be used in combination with two or more vaccine antigens obtained from the process as disclosed under embodiments of the invention. The vaccine formulations may be used with or without adjuvant(s). The vaccine formulations can be a single dose or multi dose vaccine formulations.

Poliovirus type 2 is virulent when compared to Type 1 and 3. However, capsid proteins of Type 2 are similar to that of Type 1 and 3; hence the same strategies can be followed for Type 2 as applicable to the other poliovirus serotypes for purification and inactivation. The Enterovirus is grown on Vero cell lines, in the presence of DMEM supplemented with 5% New Born Calf Serum. The viral harvest thus obtained is then clarified, filtered and purified by using two-step chromatography; SEC using Sepharose CL-6B and IEC-DEAE 650M. Alternatively, purification of the viral harvest can also be done by single chromatographic column using mixture of two different manufacturer resins that have high salt tolerance. Different anion exchanger resins like DEAE, QEAE, SP Sepharose, Poly CSX-35, CM Sepharose were used in combination with Butyl 650, Phenyl 650, Butyl Sepharose, phenyl Sepharose and aktyl Sepharose.

The concentrated bulk is then stabilized using M199 and inactivated. Sabin IPV Type-1 or Type-2 or Type-3 purified bulk is added to 2 mM Phosphate buffer having pH 7.2, 10 mM Phosphate Buffer with Saline pH 7.2 (5× diluted in inactivation) and 25 mM Sodium Acetate pH 7.2. Inactivation of the virus bulk and buffer mixture is carried out by addition of 0.025% formaldehyde at 37° C. from 0 to 13 days on magnetic stirrer.

Various vaccine formulations can be prepared with or without adjuvants. Two or more antigens obtained by the process disclosed under embodiments of the invention can be used to prepare combination vaccine compositions.

In some embodiments of the invention, the vaccine formulation prepared comprises any one of the following:
a. Base 1+D-Antigen in 2 mM PB;
b. D-Antigen in 2 mM PB+Sucrose 5% (w/v);
c. D-Antigen in 2 mM PB+Trehalose 5% (w/v);
d. D-Antigen in 2 mM PB+Maltose 5% (w/v);
e. Base 1+D-Antigen in 2 mM PB+Sucrose 5% (w/v);
f. Base 1+D-Antigen in 2 mM PB+Trehalose 5% (w/v);
g. Base 1+D-Antigen in 2 mM PB+Maltose 5% (w/v);
h. D-Antigen in 2 mM PB+Sucrose 5% (w/v)+Trehalose 5% (w/v);
i. D-Antigen in 2 mM PB+Sucrose (5% (w/v)+Maltose 5% (w/v);
j. D-Antigen in 2 mM PB+Trehalose 5% (w/v)+Maltose 5% (w/v);
k. Base 1+D-Antigen in 2 mM PB+Sucrose 5% (w/v)+Trehalose 5% (w/v);
l. Base 1+D-Antigen in 2 mM PB+Sucrose 5% (w/v)+Maltose 5% (w/v); or
m. Base 1+D-Antigen in 2 mM PB+Sucrose 5% (w/v)+Trehalose 5% (w/v)+Maltose 5% (w/v),
wherein Base 1 is 1× (9.9 g/L) concentrated M-199 with 0.5% glycine and 0.01% tween 80.

EXAMPLES

Example 1

Vero cells were revived and grown in a tissue culture flask at 37° C. The cells were passaged step by step to a higher surface area culture flask by trypsinizing the confluent monolayer. Dulbecco's Essential medium along with 5% New Born Calf Serum was used for culturing of cells. Phosphate buffered saline was used during cell expansion to remove debris, dead cells and traces of serum. After the required cells were grown, the cells were infected with enteroviruses with 0.01 MOI and incubated at 32.5° C. till complete cytopathic effect was observed. Once the cytopathic effect was observed, the harvest was collected and clarified using 0.8+0.45 u capsule filter and purified by column chromatography.

Example 2

In one embodiment of the present invention, purification is done by Single Column Purification Process in the following manner:

The purification of the viral antigens with high quality was done by using single chromatography column containing mixture of two different manufacturer resins which was tolerant to high salt concentrations there by recovering the antigenic particles with very high quality and quantity.

The single column XK16/40 was prepared by packing the column with hydrophobic resin with cation exchanger. The column height was 5 cm with a bed volume of 10 mL. Column was equilibrated with 0.2M Sodium acetate buffer (pH 4.88) and purified the viral harvest using the Akta purification system. As the column contains cation exchanger, the enteroviral particles were bound to the column in the pH range of 4.8-5.2. Later they were eluted out in the washes with pH range of 5.2-6.0.

The purified bulk was further concentrated and buffer exchanged by tangential flow filtration using 100 KDa cassettes attached to a low shear pump. The concentrated bulk was then stabilized using M199 and inactivated.

FIG. 1 to FIG. 4 depicts the quality of Poliovirus-1 and Poliovirus-3 proteins in SDS PAGE after single column chromatography and chromatogram profile showing Poliovirus-1 and Poliovirus-3 protein peaks after single column chromatography. Purity of the D-Antigen obtained is very high as evident from the above mentioned figures.

Example 3

In another embodiment of the present invention, following process was carried out to obtain high yield of the D-antigen:

1.1 Purification of Sabin IPV (sIPV)

1) Tangential flow filtration (TFF):

The clarified harvest can be quantified for D-Antigen at harvest level by ELISA. Then the clarified harvest pool was concentrated to 400×-700× using tangential flow filtration system with 100 kda cassettes and collected the retentate. Cassette was washed with phosphate buffered Saline (10 mM, pH: 7.2); then added the wash sample to retentate and used as load for column chromatography.

1.2 Two step Column Chromatography:

The purification was done by GFC using Sepharose CL-6B and then Ion Exchange Chromatography (IEC). Virus peak was collected after passing the 400×-700× TFF concentrate through gel filtration column and used as a load for DEAE 650M (Weak-Anion exchanger) using Akta purification system (GE Healthcare). Impurities were bound to the column whereas polio virus was collected in flow through with 10 mM phosphate buffer saline.

During column chromatography, peak fractions were collected and quality was assessed by SDS-PAGE analysis.

Based on the SDS gel results, pure fractions were pooled as flow through wash and D-Ag will be tested by ELISA. Hence, during inactivation with various buffers different volumes of samples were used based on the volume of flow through wash obtained.

FIG. 5 to FIG. 9 depicts the quality of PV-1, PV-2 and PV-3 proteins in SDS PAGE after two-column chromatography and chromatogram profile showing Poliovirus-1 and Poliovirus-3 protein peaks after two-step column chromatography. Yields of the D-Antigen obtained are given in the Tables 4 and 5.

Example 4

Inactivation of sIPV:

Inactivation buffer: 1× (9.9 g/L) concentrated M-199 with 0.5% glycine and 0.01% tween 80 ("Base 1") was added to make the final inactivation buffer containing 2 mM PB, 2 mM PBS or 25 mM NaOAc, so as to achieve final concentration of 1×. The final inactivation buffer containing D-Antigen was thereafter subjected to inactivation step.

An aspect of formaldehyde inactivation can occur in presence of PB buffer or PB buffer with saline or sodium acetate having concentration selected from 1 mM-100 mM, in particular 2 mM for PB and 25 mM for sodium acetate at a pH selected from (6.0-7.5) in particular between (6.9 to 7.3) and in particular at pH 7.2 adjusted by using hydrochloric acid, di-sodium hydrogen phosphate dihydrate, sodium hydroxide, acetic acid, phosphoric acid, sodium acetate trihydrate; wherein said inactivation utilizes phosphate buffer and sodium acetate. Different inactivation buffers used are given below:

TABLE 3

| Inactivation Buffers | |
|---|---|
| Inactivation Buffers | Composition |
| Base 1 | 1X (9.9 g/L) concentrated M-199 with 0.5% glycine and 0.01% tween 80 |
| Inactivation Buffer 1 | Base 1 + 2 mM PB |
| Inactivation Buffer 2 | Base 1 + 2 mM PB + 50 mM NaCl |
| Inactivation Buffer 3 | Base 1 + 2 mM PB + 100 mM NaCl |
| Inactivation Buffer 4 | Base 1 + 25 mM Sodium acetate |
| Inactivation Buffer 5 | Base 1 + 25 mM Sodium acetate + 50 mM NaCl |
| Inactivation Buffer 6 | Base 1 +25 mM Sodium acetate + 100 mM NaCl |
| Inactivation Buffer 7 | Base 1 + 50 mM Sodium acetate |
| Inactivation Buffer 8 | Base 1 + 50 mM Sodium acetate + 50 mM NaCl |
| Inactivation Buffer 9 | Base 1 + 50 mM Sodium acetate + 100 mM NaCl |
| Inactivation Buffer 10 | Base 1 + 10 mM PBS |
| Inactivation Buffer 11 | Base 1 + 10 mM PBS (5X Diluted) |
| Inactivation Buffer 12 | Base 1 + 40 mM Tris |

Inactivation agent formalin (0.025%) was added into purified virus bulk while constant mixing. Inactivation was carried out at 37° C. while continuous stirring for 13 days containing 0.22μ filtration on $6^{th}$ and $13^{th}$ day. When formaldehyde inactivation methods were particularly carried out in presence of phosphate buffer with saline and sodium acetate, significant D-antigen recoveries were observed for Sabin strains type-1, 2, 3.

Effects of buffer concentration in D-Antigen recoveries, for Type-I poliovirus, are depicted in FIG. 10 Results obtained are tabled in Table 4 below:

TABLE 4

| Poliovirus Type-1 D-Antigen recovery after Inactivation with inactivation buffers | | | | | |
|---|---|---|---|---|---|
| Buffers | Volume used (mL) | D antigen at $0^{th}$ day (DU/mL) | D antigen at $6^{th}$ day (DU/mL) | D antigen at $13^{th}$ day (DU/mL) | 0% of Recovery |
| Inactivation Buffer 1 | 20 | 1933 | 1870 | 1658 | 85.7 |
| Inactivation Buffer 2 | 20 | 1894 | 1649 | 1720 | 90.8 |
| Inactivation Buffer 3 | 20 | 2255 | 1392 | 1273 | 56.4 |
| Inactivation Buffer 4 | 20 | 1572.5 | 1140 | 1548 | 98.4 |
| Inactivation Buffer 5 | 20 | 1722 | 1059 | 952.1 | 54.3 |
| Inactivation Buffer 6 | 20 | 1536 | 1454 | 996 | 64.1 |
| Inactivation Buffer 7 | 20 | 1743 | 1271 | 1203 | 69 |
| Inactivation Buffer 8 | 20 | 1612 | 1377 | 1397 | 86.6 |
| Inactivation Buffer 9 | 20 | 2083 | 903.8 | 951.9 | 45.6 |
| Inactivation Buffer 10 | 15 | 1994 | 1313 | 1051 | 52.7 |
| Inactivation Buffer 11 | 75 | 1880 | 1519 | 1595 | 84.8 |

Table 4 above depicts the percentage of recovery in D-Antigen after inactivation from Day 0 to Day 13. It was observed that more than 90% recovery was observed in 2 mM PB, 2 mM PB with 50 mM NaCl, 25 mM Sodium Acetate, 50 mM Sodium Acetate with 50 mM NaCl and 10 mM PBS (5 times diluted) for Poliovirus Type-1 inactivated bulk.

Observation of Poliovirus Type-3 D-Antigen after Inactivation:

Inactivation Buffer 12 was selected to study the comparative inactivation as compared to the best of Inactivation Buffer obtained for Type-I poliovirus. Inactivation study was also performed for Poliovirus type-3 by choosing the best inactivation buffers based on the higher recoveries obtained for Type-1 along with comparison with Tris buffer as depicted in Table 5 below:

TABLE 5

| Poliovirus Type-3 D-Antigen recovery after Inactivation with inactivation buffers | | | | | |
|---|---|---|---|---|---|
| Buffers | Volume used (mL) | D antigen at 0 day (DU/mL) | D antigen at $6^{th}$ day (DU/mL) | D antigen at $13^{th}$ day (DU/mL) | % of Recovery D-Ag after $13^{th}$ day (DU/mL) |
| Inactivation Buffer 1 | 55 | 1391.82 | 1257 | 1266 | 91.01 |
| Inactivation Buffer-12 | | | 1366 | 1299 | 93.3 |
| Inactivation Buffer -4 | | | 1392 | 1324 | 95.1 |

Table 5 above depicts the percentage of D-Antigen recovery after inactivation from Day 0 to Day 13. It is reconfirmed that the D-Antigen recovery is more than 90% in 2 mM PB and 25 mM Sodium acetate in comparison to 40 mM Tris which is already claimed. D-Antigen Recovery during Inactivation Stages is depicted in FIG. 11.

Example 5

A key challenge in developing a purified antigenic vaccine is ensuring the stability and its efficacy during the storage of inactivated bulk. Therefore, the present study shows various excipients and its combinations for assessing the stability of inactivated D-Antigen till 30 days at 37° C. Following are the list of formulations along with its composition at the pH range of 6.0 to 7.5, at in particular 7.2.

TABLE 6

D-Antigen with various excipient

| | |
|---|---|
| Control | D-Antigen in 2 mM PB (Without stabilizers) |
| Formulation 1 | Base 1 + D-Antigen in 2 mM PB |
| Formulation 2 | D-Antigen in 2 mM PB + Sucrose 5% (w/v) |
| Formulation 3 | D-Antigen in 2 mM PB + Trehalose 5% (w/v) |
| Formulation 4 | D-Antigen in 2 mM PB + Maltose 5% (w/v) |
| Formulation 5 | Base 1 + D-Antigen in 2 mM PB + Sucrose 5% (w/v) |
| Formulation 6 | Base 1 + D-Antigen in 2 mM PB + Trehalose 5% (w/v) |
| Formulation 7 | Base 1 + D-Antigen in 2 mM PB + Maltose 5% (w/v) |
| Formulation 8 | D-Antigen in 2 mM PB + Sucrose 5% (w/v) + Trehalose 5% (w/v) |
| Formulation 9 | D-Antigen in 2 mM PB + Sucrose (5% (w/v) + Maltose 5% (w/v) |
| Formulation 10 | D-Antigen in 2 mM PB + Trehalose 5% (w/v) + Maltose 5% (w/v) |
| Formulation 11 | Base 1 + D-Antigen in 2mM PB + Sucrose 5% (w/v) + Trehalose 5% (w/v) |
| Formulation 12 | Base 1 + D-Antigen in 2mM PB + Sucrose 5% (w/v) + Maltose 5% (w/v) |
| Formulation 13 | Base 1 + D-Antigen in 2 mM PB + Sucrose 5% (w/v) + Trehalose 5% (w/v) + Maltose 5% (w/v) |

The above mentioned various formulations were used for studying the stability of the inactivated Poliovirus type-1 D-Antigen on various days till one month. These formulations comprise of inactivated polioviruses along with said buffers and excipients. This formulation step is elucidating the addition of excipients after inactivation of poliovirus was done. Following data shows the D-antigen content in DU/mL units:

TABLE 7

D-Antigen (DU/mL) at 37° C.

| | D-Antigen at 0 Day (DU/mL) | D-Antigen at 7th Day (DU/mL) | D-Antigen at 14th Day (DU/mL) | D-Antigen at 30th Day (DU/mL) |
|---|---|---|---|---|
| Control | 288.4 | 84.49 | 58.51 | 99.86 |
| Formulation 1 | | 113.61 | 103.66 | 111.14 |
| Formulation 2 | | 145.09 | 113.31 | 111.22 |
| Formulation 3 | | 148.41 | 120.38 | 126.12 |
| Formulation 4 | | 152.79 | 84.64 | 86.1 |
| Formulation 5 | | 143.66 | 133.2 | 118.93 |
| Formulation 6 | | 194.48 | 202.4 | 232.8 |
| Formulation 7 | | 256.1 | 196.35 | 140.94 |
| Formulation 8 | | 247.9 | 132.27 | 115.74 |
| Formulation 9 | | 159.03 | 123.1 | 84.84 |
| Formulation 10 | | 151.33 | 140.64 | 94.81 |
| Formulation 11 | | 167.08 | 149.37 | 114.19 |
| Formulation 12 | | 182.6 | 172.16 | 117.68 |
| Formulation 13 | | 158.77 | 164.51 | 99.13 |

Table 7 above depicts the D-Antigen stability after inactivation with various combinations of excipients from Day 0 to Day 30. It is claimed that the D-Antigen at 37° C. was most stable in Formulation 6. Effects of stabilizers in D-Antigen Recoveries are depicted in FIG. 12.

Example 6

Excipients such as stabilizers were added to the inactivation buffer, before inactivation of D-Antigen. This reduced one step in the process of vaccine development, wherein the formulation after the inactivation is not required. This also aided in achieving higher yield recovery of the D-antigen as compared to the step in which the inactivation buffer does not contain stabilizers.

Two different types of Bases were used as mentioned below:

Base 1: 1× (9.9 g/L) concentrated M-199 with 0.5% glycine and 0.01% tween 80.

Base 2: 1× (15.1 g/L) concentrated M-199+HEPES with 0.5% glycine and 0.01% tween 80.

D-antigen was formulated with Base 1 or Base 2, along with inactivation buffers and stabilizers. This was referred to as the Formulated Inactivated Buffers in Table 8 below. These formulations were thereafter subjected to inactivation and checked for virus titres.

The kinetics of infectivity of a definite virus can be studied by inactivation kinetics. Inactivation is a process of enhancing viral safety in which virus is inactivated with formalin, BPL or any other inactivating agents for particular days to reduce its infectivity. This study can determine the minimal duration of treatment to obtain a given degree of infectivity reduction. The time required for the complete inactivation depends on the concentration of formaldehyde, incubation temperature, pH of the reaction mixture and the initial concentration of the virus. Based on the results obtained from the addition of various excipients for stability, the effect of Formulation 6 was studied during the inactivation with formalin. Following are the four different compositions used for the kinetic study at the pH range of 6.0 to 7.5, in particular at 7.2, depicted in Table 8 below:

TABLE 8

Compositions of Formulated Inactivation Buffers

| | Composition |
|---|---|
| Formulated Inactivation Buffer-1 (FIB-1) | Base 1 + 2 mM PB + Trehalose (5% w/v) |
| Formulated Inactivation Buffer-2 (FIB-2) | Base 2 + 2 mM PB + Trehalose(5% w/v) |
| Formulated Inactivation Buffer-3 (FIB-3) | Base 1 + 2 mM PB |
| Formulated Inactivation Buffer-4 (FIB-4) | Base 2 + 2 mM PB |

Inactivation Kinetics of Poliovirus Type-1

Inactivation kinetics study for Poliovirus type-1 was studied by taking the samples every 24 hours from the time of inactivation till 13 days. The samples were tested for virus titration, D-Antigen and virus inactivation tests.

TABLE 9

Concentration of D-Antigen after Inactivation

| | Day 0 (BI) D-Ag/ml | Day 0 (AI) D-Ag/ml | Day 3 D-Ag/ml | Day 6 D-Ag/ml | Day 9 D-Ag/ml | Day 13 D-Ag/ml | % recovery |
|---|---|---|---|---|---|---|---|
| FIB-1 | 1454.6 | 1459.5 | 1345.9 | 1423.4 | 1321 | 1388.6 | 95.4 |
| FIB-2 | 1522.8 | 1356 | 1464 | 1482.3 | 1184.8 | 1432.8 | 94 |
| FIB-3 | 1445.5 | 1403.7 | 1102 | 1289.2 | 1278 | 1331.4 | 92.1 |
| FIB-4 | 1513.7 | 1627.5 | 1283.8 | 1283.6 | 1356.9 | 1314.8 | 86.8 |

Table 9 above shows the concentration of D-Antigen in the inactivated bulks up to 13$^{th}$ day, where the recoveries in all the inactivated buffers are more than 85%. The antigen recovery was higher with the inactivation buffers used along with the stabilizers as compared with the inactivation without stabilizers.

Inactivation Kinetics Results for Type-I:

TABLE 10

Type-1 Virus titers of Inactivated Samples

| | FIB-1 | FIB-2 | FIB-3 | FIB-4 |
|---|---|---|---|---|
| Day 0 (Before Inactivation) | $10^{9.2}$/ml | $10^{9.09}$/ml | $10^{9.37}$/ml | $10^{9.6}$/ml |
| Day 0 (After Inactivation) | $10^{7.58}$/ml | $10^{7.89}$/ml | $10^{7.57}$/ml | $10^{7.68}$/ml |
| Day 1 | $10^{5.4}$/ml | $10^{5.64}$/ml | $10^{5.22}$/ml | $10^{5.48}$/ml |
| Day 2 | $10^{3.59}$/ml | $10^{4.09}$/ml | $10^{2.66}$/ml | $10^{2.66}$/ml |
| Day 3 | 0 | 0 | 3 wells infected in $10^{-1}$ dilution | 4 wells infected in $10^{-1}$ dilution |
| Day 4 | 0 | 0 | 1 well infected in $10^{-1}$ dilution | 0 |
| Day 5 | 0 | 0 | 0 | 0 |
| Day 6 | 0 | 0 | 0 | 0 |
| Day 7 | 0 | 0 | 0 | 0 |
| Day 8 | 0 | 0 | 0 | 0 |
| Day 9 | 0 | 0 | 0 | 0 |
| Day 10 | 0 | 0 | 0 | 0 |
| Day 11 | 0 | 0 | 0 | 0 |
| Day 12 | 0 | 0 | 0 | 0 |
| Day 13 | 0 | 0 | 0 | 0 |

Table 10 above shows the titers of different component inactivated buffers after addition of formalin from $0^{th}$ day to $13^{th}$ day. The virus titers decreased till 4th day and there were no titers observed after day 5 indicating that the poliovirus was getting completely inactivated within 5 days.

Viral amplification tests were also negative for poliovirus type-1 from Day 6 to Day 13.

Example 7

Inactivation Kinetics of Poliovirus Type-3

Inactivation kinetics study for Poliovirus type-3 was studied by taking the samples every 24 hours from the time of inactivation till 13 days. The samples were tested for virus titration, D-Antigen and virus inactivation tests.

TABLE 11

| Concentration of D-Antigen after Inactivation | | | | | | |
|---|---|---|---|---|---|---|
| | Day 0 (BI) D-Ag/ml | Day 0 (AI) D-Ag/ml | Day 3 D-Ag/ml | Day 6 D-Ag/ml | Day 13 D-Ag/ml | % recovery |
| FIB-1 | 678.8 | 679.5 | 607.3 | 545.7 | 634.5 | 93.4 |
| FIB-2 | 750.7 | 669.1 | 661.7 | 670.5 | 667.4 | 88.9 |
| FIB-3 | 781.2 | 767.9 | 752.8 | 747.9 | 664.2 | 85.02 |
| FIB-4 | 722.6 | 677.8 | 642 | 672.3 | 662.7 | 91.7 |

Table 11 above shows the concentration of D-Antigen in the inactivated bulks upto $13^{th}$ day, where the recoveries in all the inactivated buffers were more than 85%.

Inactivation Kinetics Results for Type-III:

TABLE 12

| Type-3 Virus titers of Inactivated Samples | | | | |
|---|---|---|---|---|
| | FIB-1 | FIB-2 | FIB-3 | FIB-4 |
| Day 0 (Before Inactivation) | $10^{8.68}$/ml | $10^{8.67}$/ml | $10^{8.7}$/ml | $10^{8.12}$/ml |
| Day 0 (After Inactivation) | $10^{7.89}$/ml | $10^{7.89}$/ml | $10^{7.95}$/ml | $10^{7.4}$/ml |
| Day 1 | $10^{5.89}$/ml | $10^{5.86}$/ml | $10^{5.74}$/ml | $10^{4.78}$/ml |
| Day 2 | $10^{3.44}$/ml | $10^{3.77}$/ml | $10^{3.12}$/ml | $10^{3.21}$/ml |
| Day 3 | $10^{2.89}$/ml | $10^{2.8}$/ml | $10^{2.79}$/ml | $10^{2.87}$/ml |
| Day 4 | 2 wells infected in $10^{-1}$ dilution | 3 wells infected in $10^{-1}$ dilution | 3 wells infected in $10^{-1}$ dilution | 4 wells infected i n $10^{-1}$ dilution |
| Day 5 | 0 | 0 | 0 | 0 |
| Day 6 | 0 | 0 | 0 | 0 |
| Day 7 | 0 | 0 | 0 | 0 |
| Day 8 | 0 | 0 | 0 | 0 |
| Day 9 | 0 | 0 | 0 | 0 |
| Day 10 | 0 | 0 | 0 | 0 |
| Day 11 | 0 | 0 | 0 | 0 |
| Day 12 | 0 | 0 | 0 | 0 |
| Day 13 | 0 | 0 | 0 | 0 |

Table 12 above shows the titers of different component inactivated buffers after addition of formalin from $0^{th}$ day to $13^{th}$ day. The virus titers decreased till 4th day and there were no titers observed after day 5 indicating that the poliovirus is getting completely inactivated within 5 days.

Viral amplification tests were also negative for poliovirus type-3 from Day 6 to Day 13.

Example 8

D-antigen content determination by ELISA.

The D-antigen content determination was out through ELISA following the below mentioned steps:

Plate coating: The 96 well plate was coated with specific anti-polio sera in bicarbonate buffer and incubated overnight at 2-8° C.

Blocking: The plates were washed (Washing/dilution buffer –0.05% Tween 20 in 1× PBS) once and incubated at 37±1° C. for 60 minutes with block buffer (1% BSA in PBS).

Sample addition: After washing the plate with 0.05% PB ST, Serial four-fold diluted samples were added to the 96 well plate and then incubated at 37° C. for 2 hr.

Monoclonal antibody addition: The plate was washed thrice with 0.05% PBST and 1:1000 type specific monoclonal antibodies were added. The plates were sealed and incubated for 1 hour at 37° C.

Conjugate: Diluted conjugate of Anti-mouse IgG raised in goat with horse radish peroxidase at 1:2500 was added and incubated for 1 hour at 37° C.

Substrate addition: OPD substrate was added to all wells and mixture was incubated at room temperature for 20 minutes. Reaction was stopped by addition of 2M H2504. Plate was read at 490 nm. D-antigen concentration was calculated by using My assays software.

Although the invention has been illustrated and described in greater detail with reference to the preferred exemplary embodiments, the invention is not limited to the examples disclosed, and further variations can be inferred by a person skilled in the art, without departing from the scope of protection of the invention.

For the sake of clarity, it is to be understood that the use of "a" or "an" throughout this application does not exclude a plurality, and "comprising" does not exclude other steps or elements.

We claim:

1. A method for producing Enteroviral particles useful for preparation of vaccine compositions, wherein the method comprises the steps of:

a. producing Enteroviral particles in Vero cells;

b. purification of the Enteroviral particles by two step chromatography;

c. stabilization of purified Enteroviral particles; and d. chemical inactivation of the Enteroviral particles in presence of formalin (0.025%) at 37° C. for 13 days in presence of an inactivation buffer to obtain Enteroviral particles;

wherein the said method comprises addition of one or more stabilizers before the inactivation step, wherein recovery of the Enteroviral particles is in the range of 80% to 99%, and wherein the two step chromatography is carried out by first running size exclusion chromatography followed by ion exchange chromatography.

2. The method of claim 1, wherein the inactivation buffer is selected from a group comprising phosphate buffer, sodium acetate, or HEPES in presence of salt.

3. The method of claim 2, wherein the inactivation buffer comprises a buffer selected from a group of phosphate buffer; sodium acetate; salts with sodium acetate; HEPES; and M-199; glycine, and tween 80.

4. The method of claim 3, wherein the phosphate buffer is used at a concentration in the range of one of 1 mM-10 mM, and 2 mM with or without NaCl in the pH range of one of 6.0 to 7.5, and at 7.2.

5. The method of claim 3, wherein the phosphate buffer is used at a concentration in the range of one of 1 mM-10 mM, and 2 mM along with saline at a concentration of 10 mM in the pH range of one of 6.0 to 7.5, and at 7.2.

6. The method of claim 3, wherein the sodium acetate buffer is used at a concentration in the range of one of 20 mM-50 mM, and 25 mM with or without NaCl in the pH range of one of 6.0 to 7.5, and at 7.2.

7. The method of claim 6, wherein the sodium acetate buffer is used at a concentration of 25 mM having the pH of about 7.2.

8. The method of claim 1, wherein the stabilizer is selected from the group of sucrose, maltose, trehalose, human serum albumin, and M-199.

9. The method of claim 1, wherein the inactivation buffer is selected from a group of phosphate buffer sodium acetate salts with sodium acetate; and M-199 or M-199 in combination with HEPES, glycine, and tween 80.

10. The method of claim 9, wherein the phosphate buffer is used at a concentration in the range of one of 1 mM-10 mM, and 2 mM at the pH range of one of 6.0 to 7.5, and at 7.2 with one or more stabilizers.

11. The method of claim 10, wherein the one or more stabilizers is selected from a group comprising sucrose in 5% w/v concentration, M-199 in 9.9 g/L concentration, trehalose in 5% w/v concentration, and maltose in 5% w/v concentration.

12. The method of claim 10, wherein the one or more stabilizers comprises M-199 in 9.9 g/L concentration and trehalose in 5% w/v concentration.

13. The method of claim 1, wherein the Enteroviral particles are of polioviruses.

14. The method of claim 13, wherein the polioviruses are Sabin serotypes selected from one of Sabin serotypes IPV type 1, IPV type 2, and IPV type 3.

15. A method for preparing a dose reduced inactivated Polio vaccine containing Sabin polioviruses, said method comprising the steps of:

a. producing polioviruses in Vero cells;

b. purification of the polioviruses by two step chromatography;

c. stabilization of purified polioviruses by addition of M-199 medium containing glycine and tween 80;

d. inactivation of the polio viruses by using formaldehyde 0.025% at 37° C. for 13 days in presence of phosphate buffer with saline at a concentration between 2 mM to 10 mM or sodium acetate to reduce aggregation of the poliovirus particles thereby reducing the poliovirus particles losses post inactivation by greater than 90% as compared to other buffers; and e. formulating the said polio vaccine, wherein the two step chromatography is carried out by first running size exclusion chromatography followed by ion exchange chromatography.

* * * * *